United States Patent [19]

Pascavage

[11] Patent Number: 4,782,157

[45] Date of Patent: * Nov. 1, 1988

[54] PREPARATION OF SUBSTITUTED AND UNSUBSTITUTED 2-CARBAMOYL NICOTINIC AND 3-QUINOLINECARBOXYLIC ACIDS

[75] Inventor: John J. Pascavage, Morrisville, Pa.

[73] Assignee: American Cyanamid Co., Stamford, Conn.

[ * ] Notice: The portion of the term of this patent subsequent to Dec. 31, 2002 has been disclaimed.

[21] Appl. No.: 677,647

[22] Filed: Dec. 3, 1984

[51] Int. Cl.$^4$ .................. C07D 215/48; C07D 215/54; C07D 213/803; C07D 213/81

[52] U.S. Cl. .................................... 546/169; 546/316; 546/318; 546/319; 546/320

[58] Field of Search ........................ 546/169, 316, 318

[56] References Cited

FOREIGN PATENT DOCUMENTS 441707 3/1927 Fed. Rep. of Germany ...... 576/316

Primary Examiner—Richard L. Raymond
Assistant Examiner—D. B. Springer
Attorney, Agent, or Firm—H. G. Jackson

[57] ABSTRACT

The invention provides an improved process for the preparation of substituted and unsubstituted 2-carbamoyl nicotinic and 3-quinolinecarboxylic acids.

10 Claims, No Drawings

PREPARATION OF SUBSTITUTED AND UNSUBSTITUTED 2-CARBAMOYL NICOTINIC AND 3-QUINOLINECARBOXYLIC ACIDS

The reaction of unsymmetrical acid anhydrides with amines is known to proceed in a relatively unselective fashion to give mixtures of both possible isomers as illustrated in Flow Diagram I below.

FLOW DIAGRAM (I)

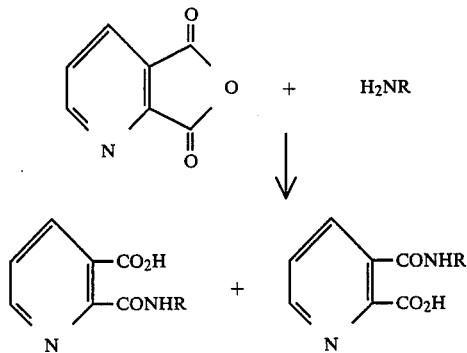

U.S. Pat. Ser. No. 539,045 of David Vincent Petrocine, filed Nov. 7, 1983 describes a method for the preparation of 2-carbamoyl nicotinic, and 2-carbamoyl-3-quinolinecarboxylic acids selectively in a solvent system containing a minimum of 4 molar equivalents of a tertiary amine such as pyridine, 4-picoline, 2-picoline, mixed picolines, quinoline and the like. This method requires the handling and recovery of relatively large quantities of these tertiary amines in order to be of use for large scale commercial production of 2-carbamoyl nicotinic and 3-quinolinecarboxylic acids.

The discovery that the addition of a catalytic amount of a tertiary amine in the presence of an organic acid improves the selectivity of the reaction between formula (II) anhydrides and formula (III) amines to give predominantly 2-carbamoyl nicotinic and 3-quinolinecarboxylic acids is unique. Previous reactions in the absence of tertiary amines yielded substantial amounts of the undesired 3-carbamoyl picolinic or quinaldic acids (>25%). The reaction of an unsymmetrical anhydride with an amine without the addition of an organic acid as described in copending U.S. Ser. No. 549,045, requires a minimum of 4 molar equivalents of the amine to obtain the desired nicotinic and 3-quinolinecarboxylic acid compounds selectively starting from the diacid.

The invention provides an improved method for the preparation of substituted and unsubstituted 2-carbamoyl nicotinic and 3-quinolinecarboxylic acids of formula (I):

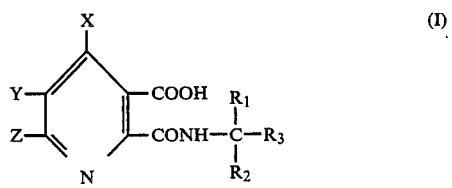

wherein $R_1$ is $C_1-C_4$ alkyl; $R_2$ is $C_1-C_4$ alkyl or $C_3-C_6$ cycloalkyl; and when $R_1$ and $R_2$ are taken together, along with the carbon to which they are attached, they may represent $C_3-C_6$ cycloalkyl optionally substituted with methyl, and when $R_1$ and $R_2$ are not the same, the optical isomers thereof; $R_3$ is CN or

W is O or S; X is hydrogen, or $C_1-C_4$ alkyl, Y is hydrogen, halogen, $C_1-C_4$ alkyl, $C_1-C_4$ alkoxy, trifluoromethyl, trichloromethyl, difluoromethoxy, diloweralkylamino, $C_1-C_4$ alkylthio, phenyl, phenoxy, or phenyl or phenoxy substituted with one $C_1-C_4$ alkyl, $C_1-C_4$ alkoxy or halogen; Z represents hydrogen, $C_1-C_4$ alkyl, trifluoromethyl, trichloromethyl, phenyl or phenyl substituted with one $C_1-C_4$ alkyl, $C_1-C_4$ alkoxy or halogen; and, when taken together, Y and Z may form a ring in which YZ are represented by the structure: $-(CH_2)_n-$, where n is an integer selected from 3 to 5, provided that X is hydrogen; or YZ is

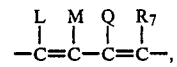

where L, M, Q and $R_7$ each represent hydrogen, halogen, $C_1-C_4$ alkyl, $C_1-C_4$ alkoxy, $C_1-C_4$ haloalkyl, difluoromethoxy, diloweralkylamino, $C_1-C_4$ alkylthio, nitro, phenyl, phenoxy, or monosubstituted phenyl or phenoxy where the substituent is one $C_1-C_4$ alkyl, $C_1-C_4$ alkoxy or halogen; with the proviso that only one of L, M, Q or $R_7$, may represent a substituent other than hydrogen, halogen, $C_1-C_4$ alkyl or $C_1-C_4$ alkoxy, comprising, reacting an anhydride of formula (II)

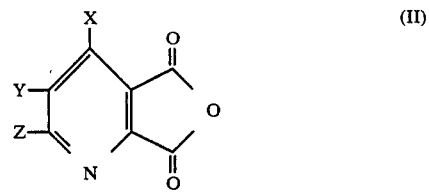

wherein X, Y and Z are as described for formula (I) above, with from 1 to 1.5 molar equivalents of an aminonitrile, aminocarboxamide or aminothiocarboxamide of formula (III)

wherein $R_1$, $R_2$ and $R_3$ are as described for formula (I) above at from 5 to 45° C. are preferably 5° to 30° C., in a solvent system containing 0.1 to less than 4 molar equivalents of a tertiary amine in the presence of 0.1 to 5 molar equivalents of an organic acid.

The above reaction may be graphically illustrated as indicated in Flow Diagram (II) below.

FLOW DIAGRAM (II)

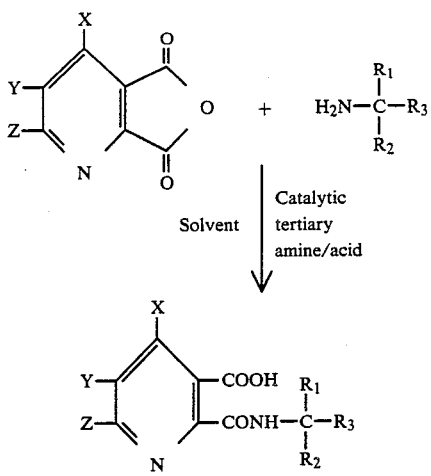

wherein X, Y, Z, R₁, R₂ and R₃ are described above.

I have found that Formula II anhydrides, below, may be selectively reacted in the presence of catalytic quantities of tertiary amines in the presence of 0.1 to 5 molar equivalents of an organic acid such as acetic acid, as demonstrated in Illustration I below.

ILLUSTRATION I

The effect of the presence of organic acid for selectively obtaining 2-carbamoylnicotinic acid utilizing catalytic quantities of 4-picoline

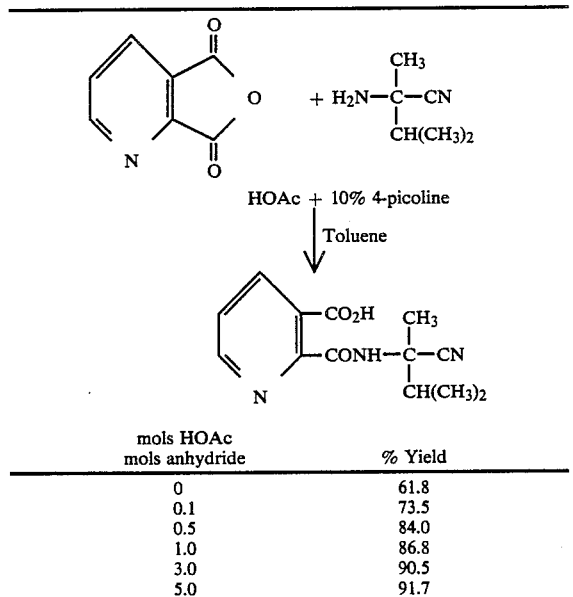

| mols HOAc mols anhydride | % Yield |
|---|---|
| 0 | 61.8 |
| 0.1 | 73.5 |
| 0.5 | 84.0 |
| 1.0 | 86.8 |
| 3.0 | 90.5 |
| 5.0 | 91.7 |

The formula (I) 2-carbamoyl nicotinic and 3-quinolinecarboxylic acids are useful intermediates in the preparation of the herbicidally effective formula (IV) 2-(4,4-disubstituted-5-oxo(or thiono)-2-imidazolin-2-yl)nicotinic acids and 3-quinolinecarboxylic acids, described in the copending application for U.S. Pat. of Marinus Los, Ser. No. 382,041 filed May 25, 1982. The method of the invention improves the isomer ratio of the desired nicotinic- and 3-quinolinecarboxylic acid isomers significantly and requires only catalytic quantities of a tertiary amine, affording the desired isomers in >80% yields. By using catalytic amounts of tertiary amines such as pyridine, 4-cyanopyridine, 4-picoline, 2-picoline, mixed picolines, triethylamine, quinoline and the like in the presence of 0.1 to 5.0 molar equivalents of organic acid such as acetic acid, and the like, I have found that the desired isomer yield is significantly improved.

The invention includes a process for the preparation of a 2-(4,4-disubstituted-5-oxo(or thiono)-2-imidazolin-2-yl)nicotinic acid and 3-quinolinecarboxylic acids of the formula:

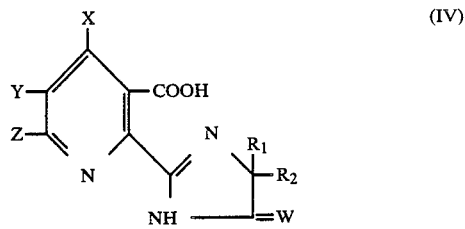

(IV)

wherein R₁, R₂, W, X, Y and Z are as defined above comprising, reacting a compound of the structure:

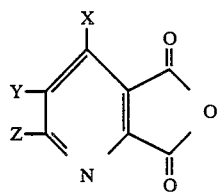

wherein X, Y and Z are as described above with a 1.0 to 1.5 equivalent, of a compound of the formula:

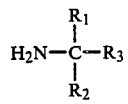

wherein R₁ and R₂ are as described above; R₃ is CN,

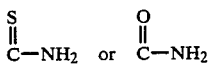

in the presence of 0.1 to less than 4 molar equivalents of a tertiary amine in the presence of 0.1 to 5.0 molar equivalents of an organic acid in the presence of a hydrocarbon co-solvent, at a temperature between 5° and 45° C. under a blanket of nitrogen, to obtain 2-carbamoyl nicotinic and 3-quinolinecarboxylic acids of formula (I) having the structure:

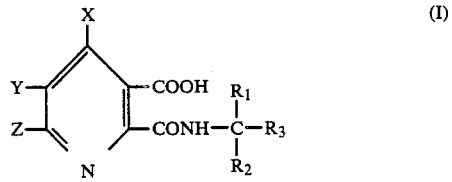

(I)

wherein X, Y, Z, R₁, R₂ and R₃ are as described above, treating the thus-formed reaction product with 2 to 10 moles of aqueous or aqueous $C_1$–$C_4$ alcoholic sodium or potassium hydroxide; and when $R_3$ is CN, hydrolyzing with either acid or 2 to 5 moles of 30 to 90% aqueous hydrogen peroxide per mole of formula (I) compound, and cyclizing under basic conditions at a temperature of 25° to 110° C.; acidifying the thus-formed reaction mixture to a pH between 1.5 and 4 with hydrochloric acid or sulfuric acid, and isolating the product by filtration or extraction of the acidified reaction mixture with an organic solvent and separating the solvent from the formula (IV) product. Since only catalytic amounts of a tertiary amine are utilized in the present invention, handling of these amines is minimized and recycling is not necessary.

The above described base cyclization of formula (I) 2-carbamoyl nicotinic and 3-quinolinecarboxylic acids to herbicidal formula (IV) 2-(4,4-disubstituted-5-oxo(or thiono)-2-imidazolin-2-yl)-nicotinic acids and 3-quinolinecarboxylic acids (Flow Diagram III, below) is described in the copending application for U.S. Letter Patent of Don W. Long, Kenneth D. Lotts and Jerry M. Barton, Ser. No. 489,480, filed May 5, 1983 and incorporated herein by reference thereto.

FLOW DIAGRAM (III)

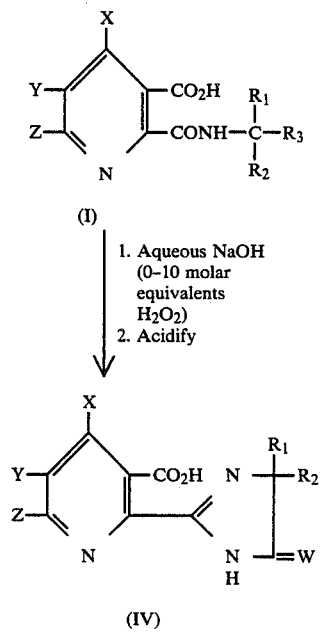

wherein X, Y, Z, $R_1$ and $R_2$ are described for formula (I).

The invention is further illustrated by the following non-limiting examples.

EXAMPLE 1

Effect of solvent on the yield of 2-[(1-cyano-1,2-dimethylpropyl)-carbamoyl]nicotinic acid

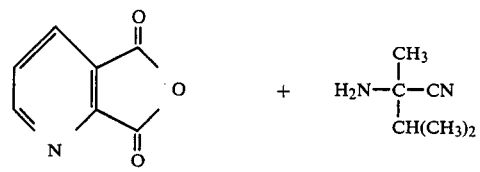

+ 2 moles HOAc + tertiary amine

↓ Toluene

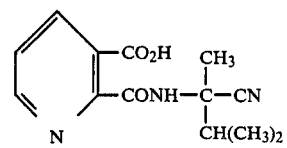

The aminonitrile (1.108 mol) is added over a ten minute period to a stirred solution of 2,3-pyridinedicarboxylic anhydride (1.0 mol) containing acetic acid (2.0 mol) in toluene, while maintaining the temperature of the reaction mixture below 25° C. Upon completion of the aminonitrile addition the reaction mixture is stirred for one and one-half hrs and then weighed and analyzed by high performance liquid chromatography for the desired 2-carbamoyl nicotinic acid.

The results of these experiments are summarized in Table I below, which demonstrates an increase in yields of the desired 2-carbamoyl nicotinic acid, utilizing catalytic amounts of a tertiary amine in the presence of acetic acid.

TABLE I

Effect of catalyst on the formation of 2-carbamoyl nicotinic acid

| Catalyst | Mol % Catalyst | % Yield |
|---|---|---|
| Pyridine | 10 | 88.4 |
| $Et_3N$ | 10 | 88.9 |
| $(n-Pr)_3N$ | 10 | 86.2 |
| NC-pyridine | 10 | 91.0 |
| 4-Picoline | 0 | 58.0 |
| 4-Picoline | 10 | 86.0 |
| 4-Picoline | 25 | 85.5 |

EXAMPLE 2

Effect of stoichiometry of 4-picoline on the formation of 2-[(1-cyano-1,2-dimethylpropyl)-carbamoyl]nicotinic acid in the absence of an acid

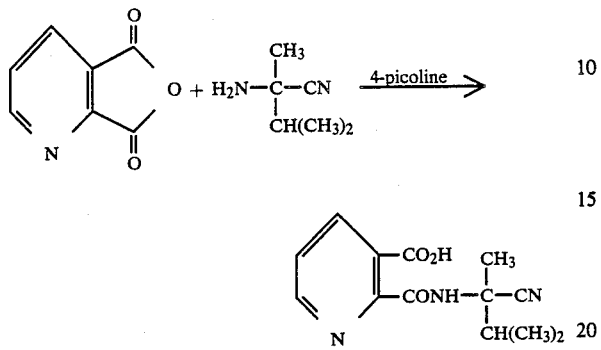

The aminonitrile (0.1375 mol) is added over a ten minute period to a stirred solution of 2,3-pyridinedicarboxylic anhydride (0.125 mol) in from 4 to 10 molar equivalents of 4-picoline while maintaining the temperature of the reaction mixture in a range between 10° and 25° C. Upon completion of the aminonitrile addition, the reaction mixture is stirred for one and one-half hrs and then weighed and analyzed by high performance liquid chromatography to determine the yield of the desired 2-carbamoyl nicotinic acid.

The results of these experiments are summarized in Table II below, which demonstrates increases in yields of the desired 2-carbamoyl nicotinic acid, utilizing from 4 to 10 equivalents of 4-picoline.

TABLE II

Effect of stoichiometry of 4-picoline on the formation of 2-carbamoyl nicotinic acid

| 4-Picoline molar equivalents | % Yield 2-carbamoyl nicotinic acid |
|---|---|
| 4.4 | 70.5 |
| 6.4 | 83.8 |
| 8.0 | 88.0 |
| 10.0 | 88.4 |

EXAMPLE 3

Preparation of 2-[(1-cyano-1,2-dimethylpropyl)carbamoly]-3-quinolinecarboxylic acid

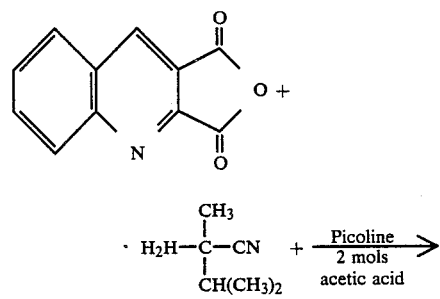

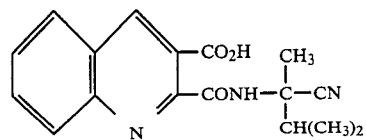

The aminonitrile (0.124 mol) is added over a 45 minutes period to a solution of 2,3-quinolinedicarboxylic anhydride (0.1 mol) in toluene (87.4 g) containing (9.3 g, 0.1 mol) of picoline and 0.22 mols of acetic acid while maintaining the reaction mixture at room temperature. The mixture is allowed to stir at room temperature for 15 minutes, to yield 91.1% of the title product. Analysis of the isomer distribution of the reaction products by high performance liquid chromatography shows a 17.4:1 ratio of the desired 2-carbamoyl-3-quinolinecarboxylic acid.

EXAMPLE 4

Effect of varying catalyst concentration of 2-[1-carbamoyl-1,2-dimethylpropyl)carbamoyl]nicotinic acid

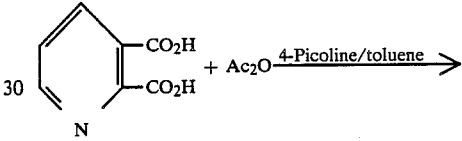

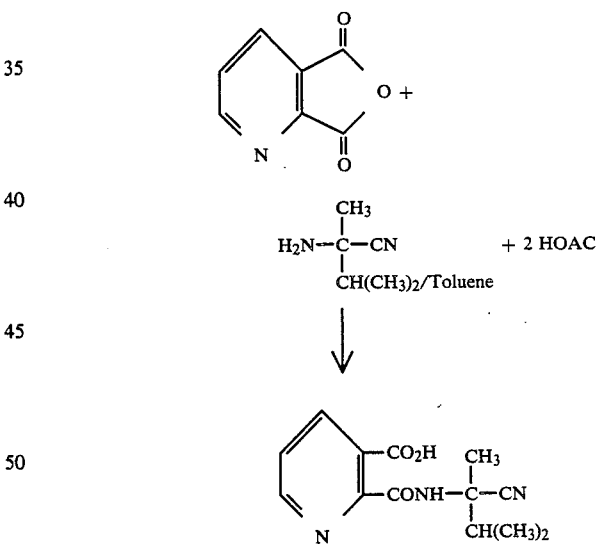

2,3-Pyridinedicarboxylic acid (167 g, 1.0 mol) is added all at once to a stirred solution of acetic anhydride (107.2 g, 1.05 mol) with varying amounts of 4-picoline in toluene under a nitrogen atmosphere. After stirring for two hours at room temperature 2-amino-2,3-dimethylbutyronitrile (1.08 mol) is added to the resulting stirred 2,3-pyridinecarboxylic anhydride solution while maintaining the temperature of the reaction mixture below 10° C. by controlling the addition rate of the aminonitrile solution. The resulting reaction mixture is stirred for one hour at 5°–10° C.

The results of these experiments utilizing varying amounts of 4-picoline are summarized in Table III below, which demonstrates the effectiveness of the use of catalytic amounts of a tertiary amine in the presence of an acid.

TABLE III

| molar equivalents picoline | [conc] picoline | % Yield |
|---|---|---|
| 3.0 | 25 | 83.5 |
| 3.0 | 10 | 87.7 |
| 2.0 | 10 | 86.1 |
| 1.5 | 10 | 84.5 |
| 1.0 | 10 | 85.6 |
| 0.5 | 10 | 83.0 |
| 0.5 | 5 | 85.2 |
| 0.3 | 4 | 83.4 |
| 0.1 | 2 | 83.1 |

EXAMPLE 5

Preparation of 2-(4-isopropyl-4-methyl-5-oxo-2-imidazolin-2-yl)nicotinic acid

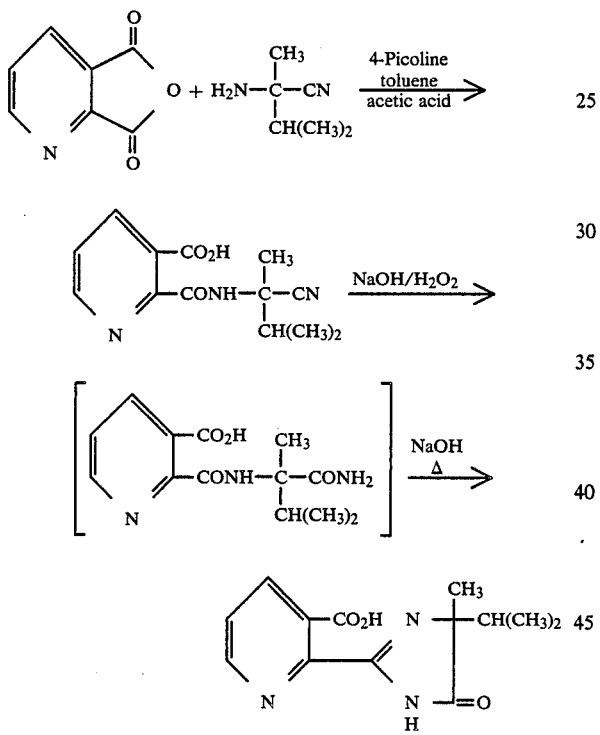

2-Amino-2,3-dimethylbutyronitrile (273.27 g, 94% purity, 2.287 mol) is added to a stirred solution of 2,3-pyridinedicarboxylic anhydride 333.3 g, 0.98 mol) in 4-picoline (1600 mL) containing 2 molar equivalents of acetic acid under a nitrogen atmosphere while maintaining the temperature of the reaction mixture at 8 to 12° C. The resulting mixture is stirred for one and one-half hours at 8° to 12° C. Analysis of the reaction mixture by high performance liquid chromatography shows the formation of the desired 2-[(1-carbamoyl-1,2-dimethylpropyl)carbamoyl]nicotinic acid in 84.1% yield. The product is isolated by dilution of the reaction mixture with toluene (1600 mL), and extraction into aqueous sodium hydroxide (800 mL, 50% NaOH, in 532 mL water) at 35° to 40° C. The basic extract is washed with toluene (1600 mL) at 35° to 40° C., and the basic solution of the product (1778.0 g) is separated off. Additional aqueous sodium hydroxide (80 g, 50%) is added to one-half of the stirred basic extract and the solution heated to 40° C. Aqueous hydrogen peroxide (221 g, 50% 6.5 mol) is then added over one hour and 15 minutes at 40° to 45° C. and the reaction mixture is allowed to stir at 40°–45° C. for two hours. The reaction mixture is then heated to 70° C. and allowed to stir for two hours to complete the formation of the 2-(4-isopropyl-4-methyl-5-oxo-2-imidazolin-2-yl)nicotinic acid which is isolated by acidification, and filtration.

EXAMPLE 6

Postemergence herbicidal evaluation of test compounds

The postemergence herbicidal activity of the compounds prepared by the process of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN ®20, a polyoxyethylene sorbitan monolaurate surfactant of Atlas Chemical Industries, in sufficient quantities to provide the equivalent of about 0.16 kg to 10 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table IV below.

| Rating System | % Difference in Growth from the Check* |
|---|---|
| 0 - No Effect | 0 |
| 1 - Possible effect | 1–10 |
| 2 - Slight effect | 11–25 |
| 3 - Moderate effect | 26–40 |
| 5 - Definite injury | 41–60 |
| 6 - Herbicidal effect | 61–75 |
| 7 - Good herbicidal effect | 76–90 |
| 8 - Approaching complete kill | 91–99 |
| 9 - Complete kill | 100 |
| 4 - Abnormal growth, that is a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (*Echinochloa crusgalli*) |
| Green foxtail | (*Setaria viridis*) |
| Purple Nutsedge | (*Cyperus rotundus* L.) |
| Wild Oats | (*Avena fatua*) |
| Quackgrass | (*Agropyron repens*) |
| Field Bindweed | (*Convolvulus arvensis* L.) |
| Cocklebur | (*Xanthium pensylvanicum*) |
| Morningglory | (*Ipomoea purpurea*) |
| Ragweed | (*Ambrosia artemisiifolia*) |
| Velvetleaf | (*Abutilon theophrasti*) |
| Barley | (*Hordeum vulgare*) |
| Corn | (*Zea mays*) |
| Rice | (*Oryza sativa*) |
| Soybean | (*Glycine max*) |
| Sunflower | (*Helianthus annus*) |
| Wheat | (*Triticum aestivum*) |

TABLE IV

"POST-EMERGENCE" TESTS: - RATES IN KG/HA

| Compound | RATE | BARN-YARDGR | GREEN FOX | P NUT-SEDGE | WILD OATS | QUACK-GRASS | FLD BINDWD | MRN-GLRY SP |
|---|---|---|---|---|---|---|---|---|
| 2-(4-Isopropyl-4- | 10.000 | 9.0 | 9.0 | 9.0 | 9.0 | | | 7.0 |
| methyl-5-oxo-2- | 2.000 | 9.0 | 9.0 | 9.0 | 9.0 | | | 8.0 |
| imidazolin-2-yl)- | 1.000 | 9.0 | 9.0 | 9.0 | 9.0 | 9.0 | 8.8 | 8.8 |
| nicotinic acid | .500 | 9.0 | 9.0 | 8.7 | 9.0 | 9.0 | 9.0 | 8.8 |
| | .250 | 8.9 | 9.0 | 8.8 | 9.0 | 9.0 | 9.0 | 8.9 |
| 2-(4-Isopropyl- | 8.000 | 9.0 | 9.0 | 9.0 | 9.0 | 9.0 | 9.0 | 9.0 |
| 4-methyl-5-oxo- | 4.000 | 9.0 | 9.0 | 9.0 | 9.0 | 9.0 | 9.0 | 8.5 |
| 2-imidazolin-2- | 2.000 | 9.0 | 9.0 | 8.5 | 9.0 | 9.0 | 9.0 | 8.3 |
| yl)-3-quinoline- | 1.000 | 9.0 | 9.0 | 8.3 | 9.0 | 8.9 | 8.7 | 8.3 |
| carboxylic acid | .800 | 9.0 | 8.8 | 6.8 | | 8.8 | 8.8 | 6.8 |
| | .500 | 8.9 | 8.9 | 7.6 | 9.0 | 8.6 | 8.3 | 7.7 |

| Compound | RATE | RAG-WEED | VELVET-LEAF | S BAR-LY LA | CORN FIELD | RICE, MATO | SOY-BEAN WI | SUNFLR XXX | S WHEAT ER |
|---|---|---|---|---|---|---|---|---|---|
| 2-(4-Isopropyl-4- | 10.000 | 9.0 | 9.0 | | | | | | |
| methyl-5-oxo-2- | 2.000 | 8.0 | 9.0 | | 9.0 | 9.0 | 9.0 | | |
| imidazolin-2-yl)- | 1.000 | 8.8 | 9.0 | 9.0 | 9.0 | 9.0 | 9.0 | 9.0 | 9.0 |
| nicotinic acid | .500 | 8.6 | 8.9 | 9.0 | 9.0 | 8.8 | 9.0 | 9.0 | 9.0 |
| | .250 | 8.6 | 8.9 | 9.0 | 9.0 | 8.8 | 9.0 | 9.0 | 9.0 |
| 2-(4-Isopropyl- | 8.000 | | 9.0 | | | | 8.5 | | |
| 4-methyl-5-oxo- | 4.000 | 9.0 | 9.0 | | 9.0 | 9.0 | 0.0 | 9.0 | 9.0 |
| 2-imidazolin-2- | 2.000 | 8.5 | 9.0 | | 9.0 | 9.0 | 0.1 | 9.0 | 9.0 |
| yl)-3-quinoline- | 1.000 | 8.8 | 8.6 | 9.0 | 9.0 | 8.7 | 3.0 | 9.0 | 8.9 |
| carboxylic acid | .800 | 8.0 | 8.3 | | | | 4.0 | | |
| | .500 | 8.4 | 7.7 | 9.0 | 9.0 | 8.3 | 2.7 | 9.0 | 8.8 |

EXAMPLE 7

Preemergence herbicidal evaluation of test compounds

The preemergence herbicidal activity of the compounds prepared by the process of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 10 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table V below. Where more than one test is involved for a given compound, the data are averaged.

TABLE V

PRE-EMERGENCE TESTS - RATES IN KG/HA

| Compound | RATE | BARN-YARDGR | GREEN FOX | P NUT-SEDGE | WILD OATS | QUACK-GRASS | FLD BINDWD | MRN-GLRY SP |
|---|---|---|---|---|---|---|---|---|
| 2-(4-Isopropyl-4- | 10.000 | 8.0 | 9.0 | 9.0 | 8.0 | | | 8.0 |
| methyl-5-oxo-2- | 2.000 | 9.0 | 9.0 | 9.0 | 9.0 | | | 8.0 |
| imidazolin-2-yl)- | 1.000 | 9.0 | 9.0 | 9.0 | 9.0 | 9.0 | 9.0 | 8.0 |
| nicotinic acid | .500 | 9.0 | 9.0 | 9.0 | 9.0 | 9.0 | 9.0 | 8.7 |
| | .250 | 9.0 | 9.0 | 9.0 | 9.0 | 9.0 | 9.0 | 8.8 |
| 2-(4-Isopropyl- | 8.000 | 9.0 | 9.0 | 9.0 | 9.0 | 9.0 | 9.0 | 8.0 |
| 4-methyl-5-oxo- | 4.000 | 9.0 | 9.0 | 9.0 | 9.0 | 9.0 | 9.0 | 9.0 |
| 2-imidazolin-2- | 1.000 | 9.0 | 9.0 | 9.0 | 9.0 | 9.0 | 9.0 | 9.0 |
| yl)-3-quinoline- | .500 | 8.8 | 9.0 | 9.0 | 8.9 | 9.0 | 9.0 | 8.6 |
| carboxylic acid | .250 | 8.3 | 8.8 | 9.0 | 8.6 | 9.0 | 9.0 | 8.0 |

| Compound | RATE | RAG-WEED | VELVET-LEAF | S BAR-LY LA | CORN FIELD | RICE, MATO | SOY-BEAN WI | SUNFLR XXX | S WHEAT ER |
|---|---|---|---|---|---|---|---|---|---|
| 2-(4-Isopropyl-4- | 10.000 | 8.0 | 8.0 | | | | | | |
| methyl-5-oxo-2- | 2.000 | 9.0 | 9.0 | | 9.0 | 9.0 | 8.0 | | |
| imidazolin-2-yl)- | 1.000 | 9.0 | 9.0 | 9.0 | 9.0 | 9.0 | 8.5 | 9.0 | 9.0 |
| nicotinic acid | .500 | 8.8 | 8.8 | 9.0 | 9.0 | 9.0 | 8.7 | 9.0 | 9.0 |
| | .250 | 8.8 | 8.8 | 9.0 | 9.0 | 9.0 | 8.7 | 9.0 | 9.0 |
| 2-(4-Isopropyl- | 8.000 | 9.0 | 8.0 | | | | | | |
| 4-methyl-5-oxo- | 4.000 | 9.0 | 9.0 | | 9.0 | 9.0 | | 9.0 | 9.0 |
| 2-imidazolin-2- | 1.000 | 9.0 | 8.8 | 9.0 | 9.0 | 9.0 | 6.5 | 9.0 | 9.0 |
| yl)-3-quinoline- | .500 | 8.8 | 8.5 | 9.0 | 9.0 | 9.0 | 4.0 | 8.7 | 8.9 |
| carboxylic acid | .250 | 7.9 | 7.9 | 9.0 | 8.8 | 9.0 | 3.6 | 8.6 | 8.6 |

What is claimed is:

1. In a method for the preparation of substituted and unsubstituted 2-carbamoyl nicotinic and 3-quinolinecarboxylic acids of formula (I):

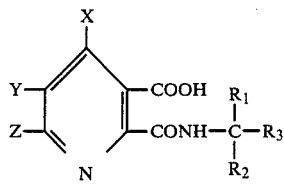

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together along with the carbon to which they are attached, they may represent $C_3$–$C_6$ cycloalkyl optionally substituted with methyl, and when $R_1$ and $R_2$ are not the same, the optical isomers thereof; $R_3$ is CN or

W is O or S; X is hydrogen, or $C_1$–$C_4$ alkyl, Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, phenyl or phenoxy or phenyl or phenoxy substituted with one $C_1$–$C_4$ alkyl, $C_1$–$C_4$ alkoxy or halogen; Z represents hydrogen, $C_1$–$C_4$ alkyl, trifluoromethyl, trichloromethyl, phenyl or phenyl substituted with one $C_1$–$C_4$ alkyl, $C_1$–$C_4$ alkoxy or halogen; and when taken together, Y and Z may form a ring in which YZ are represented by the structure: —(CH$_2$)$_n$—, where n is an integer selected from 3 to 5, provided that X is hydrogen; or YZ is

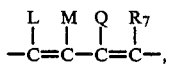

where L, M, Q and $R_7$ are each of hydrogen, halogen, $C_1$–$C_4$ alkyl, $C_1$–$C_4$ alkoxy, $C_1$–$C_4$ haloalkyl, difluoromethoxy, diloweralkylamino, $C_1$–$C_4$ alkylthio, nitro, phenyl, phenoxy or mono-substituted phenyl or phenoxy where the substituent is one $C_1$–$C_4$ alkyl, $C_1$–$C_4$ alkoxy or halogen; with the proviso that only one of L, M, Q or $R_7$, may represent a substituent other than hydrogen, halogen, $C_1$–$C_4$ alkyl or $C_1$–$C_4$ alkoxy, comprising reacting an anhydride of formula (II)

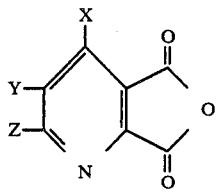

wherein X, Y and Z are as described above with from 1.0 to 1.5 molar equivalents of an aminonitrile, aminocarboxamide, or aminothiocarboxamide of formula III:

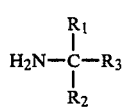

wherein $R_1$, $R_2$ and $R_3$ are as described above at from 5° to 45° C., the improvement comprising carrying out the reaction in the presence of 0.1 to 4 molar equivalents of a tertiary amine and 0.1 to 5.0 molar equivalents of an organic carboxylic acid in an organic solvent.

2. A method according to claim 1, wherein the tertiary amine is the pyridine, 4-cyanopyridine, 4-picoline, 2-picoline, mixed picolines, triethylamine, tripropylamine or quinoline.

3. A method according to claim 2, wherein the reaction solvent is toluene.

4. A method according to claim 3, wherein the acid is acetic acid.

5. A method according to claim 4, wherein the reaction is conducted in a temperature range of 5° to 30° C.

6. A method according to claim 5, for the preparation of 2-[(1-carbamoyl-1-2-dimethylpropyl)carbamoyl]-nicotinic acid.

7. A method according to claim 5, for the preparation of 2-[(1-carbamoyl-1,2-dimethylpropyl) carbamoyl]3-quinolinecarboxylic acid.

8. A method according to claim 5, for the preparation of 2-[(1-cyano-1,2-dimethylpropyl)carbamoyl]nicotinic acid.

9. A method according to claim 5, for the preparation of 2-[(1-cyano-1,2-dimethylpropyl)carbamoyl]3-quinolinecarboxylic acid.

10. In a process for the preparation of a 2-(4,4-disubstituted-5-oxo(or thiono)-2-imidazolin-2-yl)-nicotinic acid and 3-quinolinecarboxylic acids of the formula:

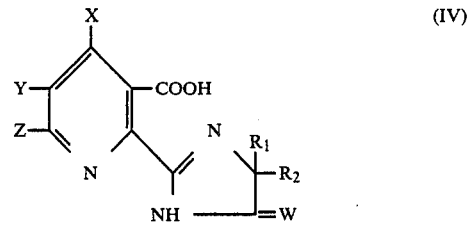

wherein $R_1$ is $C_1$–$C_4$ alkyl; $R_2$ is $C_1$–$C_4$ alkyl or $C_3$–$C_6$ cycloalkyl; and when $R_1$ and $R_2$ are taken together along with the carbon to which they are attached, they may represent $C_3$–$C_6$ cycloalkyl optionally substituted with methyl, and when $R_1$ and $R_2$ are not the same, the optical isomers thereof; W is O or S; X is hydrogen, or $C_1$–$C_4$ alkyl, Y is hydrogen, halogen, $C_1$–$C_4$ alkyl, $C_1$–$C_4$ alkoxy, trifluoromethyl, trichloromethyl, difluoromethoxy, diloweralkylamino, $C_1$–$C_4$ alkylthio, nitro, phenyl or phenoxy optionally substituted with one $C_1$–$C_4$ alkyl, $C_1$–$C_4$ alkoxy or halogen; Z is hydrogen $C_1$–$C_4$ alkyl, trifluoromethyl, trichloromethyl, phenyl or phenyl substituted with one $C_1$–$C_4$ alkyl, $C_1$–$C_4$ alkoxy or halogen; and when taken together, Y and Z may form a ring in which YZ are represented by the structure: —(CH$_2$)$_n$—, where n is an integer from 3 to 5, provided that X is hydrogen; or YZ is

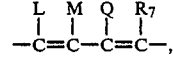

where L, M, Q and $R_7$ are each of hydrogen, halogen, $C_1$–$C_4$ haloalkyl, difluoromethoxy, diloweralkylamino, $C_1$–$C_4$ alkylthio, nitro, phenyl, phenoxy or mono-substituted phenyl or phenoxy where the substituent is $C_1$–$C_4$ alkoxy or halogen; with the proviso that only one of L, M, Q or $R_7$, may represent a substituent other than hydrogen, halogen, $C_1$-$C_4$ alkyl or $C_1$-$C_4$ alkoxy; comprising, reacting a compound of the structure:

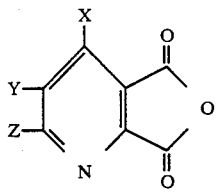

wherein X, Y and Z are as described above with a 1.0 to 1.5 equivalent, of a compound of the formula:

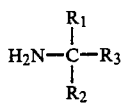

wherein $R_1$ and $R_2$ are as described above; $R_3$ is CN,

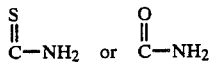

in the presence of a hydrocarbon cosolvent, at a temperature between 5° and 45° C. under a blanket of nitrogen, to obtain 2-carbamoyl nicotinic and 3-quinolinecarboxylic acids of formula (I) having the structure:

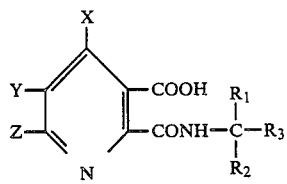

wherein X, Y, Z, $R_1$, $R_2$ and $R_3$ are as described above, treating the thus-formed reaction product with 2 to 10 moles of aqueous or aqueous $C_1$-$C_4$ alcoholic sodium or potassium hydroxide; and when $R_3$ is CN, hydrolyzing with either acid or 2 or 5 moles of 30 to 90% aqueous hydrogen peroxide per mole of formula (I) compound, and cyclizing under basic conditions at a temperature of 25° to 110° C., acidifying the thus-formed reaction mixture to a pH between 1.5 and 4 with hydrochloric acid or sulfuric acid, and isolating the product by filtration or extraction of the acidified reaction mixture with an organic solvent and separating the solvent from the formula (IV) product the improvement comprising carrying out the reaction for preparing the formula I product in the presence of 0.1 to 4 molar equivalents of a tertiary amine in the presence of 0.1 to 5.0 molar equivalents of an organic carboxylic acid.

* * * * *